US010918620B2

(12) United States Patent
Rosenberg Messina

(10) Patent No.: US 10,918,620 B2
(45) Date of Patent: Feb. 16, 2021

(54) USE OF STATINS FOR PERIODONTAL DISEASE AND BONE REGENERATION

(71) Applicant: David Rafael Rosenberg Messina, Las Condes (CL)

(72) Inventor: David Rafael Rosenberg Messina, Santiago (CL)

(*) Notice: Subject to any disclaimer, the term of this patent is extended or adjusted under 35 U.S.C. 154(b) by 0 days.

(21) Appl. No.: 15/856,660

(22) Filed: Dec. 28, 2017

(65) Prior Publication Data

US 2018/0153856 A1 Jun. 7, 2018

Related U.S. Application Data

(63) Continuation of application No. 14/417,106, filed as application No. PCT/IB2013/056791 on Aug. 21, 2013, now abandoned.

(60) Provisional application No. 61/692,087, filed on Aug. 22, 2012.

(51) Int. Cl.
| | | |
|---|---|---|
| *A61K 31/40* | (2006.01) |
| *A61K 8/49* | (2006.01) |
| *A61K 31/22* | (2006.01) |
| *A61K 31/366* | (2006.01) |
| *A61K 31/405* | (2006.01) |
| *A61K 31/4418* | (2006.01) |
| *A61Q 11/00* | (2006.01) |
| *A61K 9/00* | (2006.01) |

(52) U.S. Cl.
CPC .............. *A61K 31/40* (2013.01); *A61K 8/498* (2013.01); *A61K 8/4913* (2013.01); *A61K 9/0063* (2013.01); *A61K 31/22* (2013.01); *A61K 31/366* (2013.01); *A61K 31/405* (2013.01); *A61K 31/4418* (2013.01); *A61Q 11/00* (2013.01)

(58) Field of Classification Search
CPC ...... A61K 8/498; A61K 8/4913; A61K 31/22; A61K 9/0063; A61K 31/366; A61K 31/405; A61K 31/4418; A61K 31/40; A61P 43/00; A61Q 11/00
See application file for complete search history.

(56) References Cited

U.S. PATENT DOCUMENTS

| | | |
|---|---|---|
| 5,244,916 A | 9/1993 | Bokoch |
| 6,300,377 B1 | 10/2001 | Chopra |
| 6,376,476 B1 | 4/2002 | Gasper et al. |
| 2004/0254238 A1 | 12/2004 | Garrett et al. |
| 2005/0084489 A1 | 4/2005 | Wilder et al. |
| 2008/0280980 A1 | 11/2008 | Van Dyke |
| 2010/0152275 A1 | 6/2010 | Fromm et al. |
| 2012/0101061 A1 | 4/2012 | Gjorstrup et al. |
| 2014/0186271 A1 | 7/2014 | Quivey, Jr. |

FOREIGN PATENT DOCUMENTS

| | | |
|---|---|---|
| WO | 9825460 A1 | 6/1998 |
| WO | 9945923 A1 | 9/1999 |
| WO | 0152829 A2 | 7/2001 |
| WO | 0174180 A1 | 10/2001 |
| WO | 2004091626 A1 | 10/2004 |

OTHER PUBLICATIONS

International Search Report by the International Searching Authority for the International Application No. PCT/IB2013/056791, dated Feb. 20, 2014 (3 pages).
Written Opinion by the International Searching Authority for the International Application No. PCT/IB2013/056791, dated Feb. 20, 2014 (6 pages).
International Preliminary Report on Patentability by the International Searching Authority for the International Application No. PCT/IB2013/056791, dated Feb. 24, 2015 (7 pages).
Supplementary European Search Report by the European Patent Office for the European Patent Application No. EP 13 83 0936, dated Nov. 19, 2015 (3 pages).
European Search Opinion by the European Patent Office for the European Patent Application No. EP 13 83 0936, dated Nov. 19, 2015 (5 pages).
Meisel, et al., ISRN Dentistry, "Cholesterol, C-Reactive Protein, and Periodontitis: HMG-CoA-Reductase Inhibitors (Statins) as Effect Modifiers", vol. 2011 (7 pages).
Subramanian, et al., Journal of the American College of Cardiology, "High-Dose Atorvastatin Reduces Periodontal Inflammation", vol. 62, No. 25, 2013 (10 pages).
Sirtori, Pharmacological Research, "The Pharmacology of Statins", vol. 88, 2014 (9 pages).
Bellosta, et al., Circulation, "Safety of Statins: Focus on Clinical Pharmacokinetics and Drug Interactions", vol. 109, supplement III, 2004 (9 pages).

(Continued)

*Primary Examiner* — Lezah Roberts
(74) *Attorney, Agent, or Firm* — Daniel F. Nesbitt; Hasse & Nesbitt LLC

(57) ABSTRACT

The present invention discloses topical compositions comprising at least one statin as the main active compound for primary prevention or treatment of periodontal disease, for complementing standard treatment of periodontal disease, and for bone regeneration. The topical compositions are formulated for example, but not limited to, as toothpaste, mouthwash, tablets to dissolve in the mouth, elements or devices for intraoral slow-release of statins, dental floss, gel for being applied in dental trays, concentrated gel for irrigation of periodontal pockets, fluid (for example in blisters), powder, powder or liquid for preparing a solution, and gel. The present invention also discloses method for primary prevention or treatment of periodontal disease, for complementing standard treatment of periodontal disease, and for bone regeneration, comprising administering the topical compositions in the different formulations to a subject in need thereof.

3 Claims, 1 Drawing Sheet

(56) References Cited

OTHER PUBLICATIONS

Diaz Rodriguez, et al., Clinica E Investigacion en Arteriosclerosis, "Pitavastatina: A New Alternative in the Treatment of Dyslipidemia", vol. 24, No. 1, 2012 (10 pages).
Garcia-Sabina, et al., Farmacia Hospitalaria, "Specific Considerations in the Prescription and Therapeutic Interchange of Statins", vol. 36, No. 2, 2012 (12 pages).
Arguedas Quesada, Revista Costarricense de Cardiologia, "Actualization en Farmacoterapia—La Farmacologia de las Estatinas—Primera Parte", vol. 4, No. 1, 2002 (11 pages).

USE OF STATINS FOR PERIODONTAL DISEASE AND BONE REGENERATION

TECHNICAL FIELD

The present invention is related to the use of topical compositions comprising statins as the main active compound in different formulations for primary prevention or treatment of periodontal disease, for complementing standard treatment of periodontal disease and for bone regeneration.

BACKGROUND ART

Chemical Control of Periodontal Diseases.

Role and utility of topically applied chemicals have been intensely investigated in periodontics as a complement to mechanical procedures for controlling plaque, associated with prevention and adjunctive treatment of periodontal disease.

Mouthwashes.

The oral rinses, regardless of the chemical agent used, do not significantly penetrate into the sulcus and/or periodontal pocket (0.2 mm), so its action is limited to the control of supragingival plaque and gingivitis therapeutic management. Neither the level of probing depth nor attachment level is significantly altered.

The most researched and effective antiplaque agent is chlorhexidine.

Chemically chlorhexidine corresponds to a bisbiguanidine with cationic properties. The molecule is symmetrical, with two chlorophenyl rings and two biguanidine groups connected by a central hexamethylene chain.

The interaction between the positively charged molecule of chlorhexidine and negative charges that are found in bacterial cell wall has been shown. This increases the cell permeability losing osmotic balance thereby producing bacterial lysis. It also reduces the formation of the pellicle on the tooth surface and disrupts bacterial adhesion.

An important property of chlorhexidine is its high substantivity, i.e. the long association between a material and a substrate, even longer than would be expected with a simple mechanical deposition. This promotes slow release of the agent to the medium.

In the case of chlorhexidine, their substantivity is 12 hours at a concentration of 0.12%. It is therefore considered an effective antibacterial, bactericidal in high concentrations and bacteriostatic in low concentrations as gradually diluted in saliva.

Clinical results with regard to decreased levels of supragingival bacterial plaque and gingival inflammation are 55% and 45% respectively. Early clinical studies employed a solution of 10 ml at 0.2% equivalent to 20 mg of chlorhexidine per use. Currently, according to the recommendation of American Dental Association (ADA), 15 ml at 0.12% equivalent to 18 mg of chlorhexidine are used. The amount of the agent per use is almost the same and clinical results are similar. Its minimum inhibitory concentration (MIC) is 8 to 500 mg/ml, studied for 52 bacteria isolated from subgingival plaque. At a concentration of 250 mg/ml all bacteria isolated from patients with periodontitis were inhibited. MICs were all lower than the level achieved by applying topically. Antimicrobial resistance with chlorhexidine has not been detected.

Adverse effects described include appearance of staining effects associated with certain foods and prolonged use of the antiseptic, temporary alteration of taste and relative increase in deposits of calculus.

Its indications are primarily as an adjunct to mechanical oral hygiene phase in periodontal treatment, when an effective and adequate mechanical control of plaque (post-surgical procedures including periodontal surgery, intermaxillary fixation, in individuals mental and/or physically disabled) is real difficulty for the patient to achieve, patients with systemic compromise, with a predisposition to oral infections as candidiasis always associated with a specific antifungal therapy, immunocompromised patients, in patients at high risk of cavities development (under strict control and prevention program) to reduce the likelihood of bacteremia during surgical procedures (note that chlorhexidine value is higher when it is used before oral complications in patients systemically compromised and that its use is not considered as a monotherapy) in recurrent oral ulcers, fixed and removable braces, in implants.

Many substances have some degree of antimicrobial efficacy "in vitro", but their use in clinic as a mouthwash are totally impractical because it would be necessary to rinse ten times a day, due to their lack of substantivity and that they are rapidly diluted and removed by saliva. Agents that do not exhibit this property of substantivity are classified as first generation agents (certain antibiotics, quaternary ammonium compounds, phenolic compounds, fluorine compounds, oxygenating agents, povidone-iodine). Among the phenolic compounds the only product that has been studied is Listerine®, which compositions includes thymol essential oils, menthol, eucalyptol and methyl salicylate. The alcoholic vehicle of this agent reaches an extremely high concentration of 26.9% with a pH of 5.0. This explains the adverse effects associated with burning sensation resulted from epithelial damage and ulceration of the mucous and significant alterations in taste.

Chemical agents of second generation are characterized by a high substantivity (retention of 25 to 30% after each mouthwash for one minute). Such compounds are active in situ during hours (chlorhexidine, fluoride amines, triclosan, when combined with certain compounds). Triclosan is a bisphenol antiseptic, nonionic, with low toxicity and wide antibacterial spectrum. Because it does not bind well to oral surfaces because it lacks of a strong positive charge, formulations that increase their ability to bind to the plaque and the tooth have been created (combination with zinc citrate to increase its antiplaque and anticalculus potential, incorporation of a copolymer of methoxyethylene and maleic acid to increase its retention time). Triclosan at concentrations of 0.2-0.5% and zinc citrate at 0.5-1% favor a significant reduction in plaque and gingivitis. The same effect has been achieved with dentifrices containing 0.3% triclosan and 0.25% of copolymer of methoxyethylene and maleic acid. Mouthwash formulations at 0.3% have shown significant reductions in plaque and gingivitis. Importantly, zinc citrate has a limited effect on bacterial growth on surfaces that have been originally clean but has a great effect on areas with moderate amounts of plaque. This indicates that the major effect of zinc citrate is to reduce the rate of bacterial proliferation in plaque already formed. By contrast, triclosan has a great effect on surfaces free of plaque after brushing and decreases its antibacterial potential with increasing of existing plaque. This supports the hypothesis that triclosan may be adsorbed to the tooth surface and may prevent bacterial adhesion or inhibit the growth of bacteria that colonize the surface.

Antibacterial substances with little effect but that interfere with bacterial adhesion are agents referred to as 3rd generation (aminoalcohols: octapinol, decapinol). It has been shown that the use of these elements as supplements to oral hygiene measures reduces the formation of bacterial plaque compared with a placebo mouthwash. However, from the clinical point of view, second generation antibacterial agents remain of first choice.

Antibiotics are not indicated for the control of bacterial plaque. Their potential adverse effects exceed their possible therapeutic value and are not effective in controlling supragingival plaque and in gingivitis treatment.

Irrigation.

The use of irrigation devices can increase the capacity of the products for reaching the subgingival area, however, several studies have concluded that in general the irrigation at the gingival margin is not very efficient in achieving a sufficiently apical extent with respect to subgingival plaque, even when the tip of the irrigator is placed 3 mm inside the pocket. Currently, electrical and mechanical oral irrigating apparatus have been designed, having a low predictability in reaching the full depth of the gingival crevice, both in shallow and depth sites.

The effectiveness of subgingival irrigation is limited by the action of crevicular fluid causing a rapid clearance of irrigant, by the presence of blood components that inactivate the solution, and by the presence of subgingival calculus which hinders the penetration of the agent.

From the microbiological point of view, subgingival irrigation by itself can temporarily altering the bacterial composition, however, within the first eight weeks there is a complete recurrence of original subgingival bacteria levels. The possible reduction of spirochetes and mobile *bacillus* after a professional irrigation can be attributed to frequent mechanical disruption rather than the effect of the used agent by itself. Similarly, these microbiological changes have no effect on bleeding, attachment level probing depth and do not stop the progression of periodontal disease.

Clinical results (periodontitis) obtained with mechanical instrumentation (root planing) are not exceeded when associated subgingival irrigation, independent of the chemical agent used. The only function is the mechanical drag. With the exception of high concentrations of chlorhexidine (2%) or tetracycline (10%) and only when applied for more than 5 minutes, addition of antimicrobial agents in the irrigating solution adds no benefit to that obtained when using only water or saline.

During the maintenance phase of a treated patient, daily irrigation can improve oral hygiene and gingival health of patients with a low level of mechanical control of plaque. However, this does not mean that irrigations prevent the repopulation of the site with pathogenic bacteria or modify the intervals between maintenance sessions. For this reason, sulcus irrigation cannot replace the professional mechanical instrumentation during control of periodontal support.

Toothpastes.

The main functions of a dentifrice (in addition to brushing) are: reducing the amount of plaque, reducing the risk of cavities, remove dental stains, remove food debris and improve breath. The benefits sought are directly influenced by the action of the principal agent and its relationship with other compounds, whether of the same formulation or from other sources. Toothpastes contain a number of compounds which serve the above purposes:

1. Abrasive agent (must clean and polish without causing damage to enamel, dentin and mucous; must be insoluble, inert, nontoxic and preferably white; calcium carbonate, alumina, silica are currently used; the size, shape and hardness of the particle is important).
2. Filler (provides stability and consistency; may be soluble or insoluble in water; alginates, sodium carboxymethylcellulose, sodium magnesium, and others are used).
3. Surfactant (Aids in dispersing of food remains and others; the most widely used is sodium lauryl sulfate which also has antibacterial properties and helps with solubilization of key ingredients such as flavorings and certain antibacterial agents).
4. Wetting agent (aids in reducing moisture loss and improves product texture in the mouth).
5. Flavors.
6. Therapeutic agents (anticavities, antiplaque, for reducing dentinal hypersensitivity and bleaching agents).

At present there are formulations of pastes or gels whose main chemical agent is triclosan or chlorhexidine. The effectiveness of chlorhexidine gel depends on the patient's ability to achieve effective mechanical control of bacterial plaque, i.e. the patient's ability to bring the gel to the appropriate sites of the mouth. The chlorhexidine gel does not readily penetrate the areas distant from the site of application, in this manner; some effectiveness of the gel depends on the correct amount that it reaches in appropriate areas of the mouth and its stay for a long period.

There are gels with a concentration of 0.1% and 1% chlorhexidine. Considering a dilution of the agent by the action of the saliva during brushing, then the actual concentration of chlorhexidine is lower.

Toothpaste based on a combination of triclosan—copolymer, according to studies, shows a reduction of approximately 20-30% in levels of gingival index and bacterial plaque. Efficacy in the reduction of cavities is similar to that achieved with conventional fluoride toothpaste.

Dentifrices containing soluble pyrophosphates or zinc compounds have demonstrated a reduction between 10% and 50% of dental calculus deposits. Studies describe that the presence of pyrophosphates do not alter the bioavailability of the fluoride in toothpaste.

Dentine Hypersensitivity.

A significant number of chemical agents for the treatment of dentine hypersensitivity have been incorporated into toothpastes. Some of these, accepted by the American Dental Association (ADA) are strontium chloride and potassium nitrate. They should be used for a period not less than 12 weeks to reach a significant desensitizing effect accompanied by an effective mechanical control of plaque. As a result of better plaque control level, sensitivity and the consequences of the action of the plate are small.

In conclusion, the preventive measures to maintain a periodontal health and therapeutic actions used to treat gingivitis and periodontitis are based on the elimination and control of plaque.

The more effective plaque control is mechanical removal by practicing proper technique of brushing and flossing, and professional prophylaxis.

The combination of chemicals with mechanical removal in oral hygiene offers an advantage because the higher concentration of bacterial load can be reduced mechanically, leaving a number of disorganized and thin plaque that can be removed with chemicals.

However, when trying to intraorally use a drug with antibacterial effects, it should be considered its strict and real need and indication and some major problems as the development of allergic reactions, toxic effects and the development of resistant bacteria. Chlorhexidine, for its properties and performance is still the safest and more efficient anti plaque chemical.

In terms of evaluation, triclosan has caused great interest in recent years. Subgingival irrigation as a treatment modality compared with mechanical instrumentation is less effective and less significant on clinical parameters associated with periodontitis.

For subgingival irrigation has an important role in the treatment of periodontal disease it is necessary to have a significant and sustained effect on the bacterial composition, achieve long-term positive effect on clinical parameters of periodontitis and a beneficial effect beyond the achieved effect with root planing alone.

There are several products for the management of bacterial plaque, reduction in calculus formation and dentine hypersensitivity. The clinical choice of these compounds should be based on scientific validity and its relationship to the real needs of the patient.

Statins

Statins are drugs that have been widely used to treat hypercholesterolemia in patients at high risk of developing atherosclerosis and have episodes of cardiovascular disease. Statins are potent cholesterol lowering agents that inhibit cholesterol biosynthesis in the liver and consequently have proved beneficial effects in the primary and secondary prevention of ischemic heart disease. These drugs inhibit the enzyme 3-hydroxy-3-methylglutaryl Coenzyme A reductase (HMG CoA reductase) (Essig, M et al. 3-hydroxi-3-methylglutaryl coenzyme A reductase inhibitors increase fibrinolytic activity in rat aortic endothelial cells. Circ. Res. 1998; 83:683-690), responsible for the conversion in the liver of HMG-CoA to mevalonic acid, the precursor of cholesterol, which results in a reduced levels of low density cholesterol (LDL) and other changes in lipid profile (Essig, M et al. 3-hydroxi-3-methylglutaryl coenzyme A reductase inhibitors increase fibrinolytic activity in rat aortic endothelial cells. Circ. Res. 1998; 83:683-690).

HMG CoA reductase responds to a negative feedback regulation given by the steroidal and nonsteroidal products of mevalonate metabolism, by decreasing the expression of the reductase gene. Statins reduce the cholesterol content of hepatocytes and increase the expression of LDL receptors by inhibiting HMG CoA reductase (Vaughan, C J. et al. The evolving role of statins in the management of atherosclerosis. J. Am. Coll. Cardiol. 2000; 35:1-10). These receptors are responsible for receptor-mediated endocytosis of LDL cholesterol, thus, decreasing the plasma level of circulating LDL.

The different types of statins such as atorvastatin, simvastatin, lovastatin, fluvastatin, pravastatin, among others, differ among themselves in absorption, plasma protein binding, excretion and solubility, exhibiting a wide dose-dependent efficacy in reducing LDL.

Statins also cause a small reduction in triglyceride levels (5-10%), along with small increases in HDL cholesterol levels (5-10%) (Vaughan, C J. et al. The evolving role of statins in the management of atherosclerosis. J. Am. Coll. Cardiol. 2000; 35:1-10).

On the other hand, adverse effects associated with statin therapy are generally mild, transient and reversible. These include: dyspepsia, abdominal pain and flatulence. However, the most important adverse effects are elevated serum transaminases and the development of myositis. The risk of myositis increases in patients receiving statin treatment with gemfibrozil, nicotinic acid or macrolides and cyclosporine. The administration of drugs that inhibit cytochrome P450, such as anti fungal azolics, cimetidine and methotrexate, also increase the likelihood of adverse effects, if consumed along with statins (Vaughan, C J. et al. The evolving role of statins in the management of atherosclerosis. J. Am. Col. Cardiol. 2000; 35:1-10).

Statins are first attributed anti-inflammatory properties that counteract the inflammation that produces atherosclerosis, besides from their lipid lowering properties, and then, with its use, also ascribed to other properties such as increased bone mineral density and reduced fracture risks.

This inflammatory process is induced by free radicals, proinflammatory cytokines and lack of nitric oxide. Statins increase levels of bioavailable nitric oxide (endogenous vasodilator) and decreased proinflammatory cytokines (e.g. TNF-α, a tumor necrosis factor and IL-6) up to 20% (Musial, J. et al. Anti-inflammatory effects of simvastatin in subjects with hypercholesterolemia. Int. J. Cardiol. 2001; 77:247-253), reducing the effects of inflammation.

Another marker of inflammation and in parallel has proven to be a marker of coronary heart disease risk is C-reactive protein (CRP), proinflammatory protein that measures liver inflammation indices. The use of statins has shown to reduce CRP levels in the blood, thus decreasing the risk of heart disease.

The effects observed with statins are higher than expected as a unique change in the levels of blood lipids. This suggests the existence of additional nonlipidic effects responsible for its complex pharmacological profile demonstrated in clinical trials. Consistent with this, recent studies have shown various effects of statins on nonlipidic biological scopes known as "pleiotropic effects" of statins, which include the following:

Atherosclerosis regression (Vaughan, C J. et al. The evolving role of statins in the management of atherosclerosis. J. Am. Coll. Cardiol. 2000; 35:1-10), reducing mortality and morbidity caused by cardiovascular diseases (Vaughan, C J. et al. The evolving role of statins in the management of atherosclerosis. J. Am. Coll. Cardiol. 2000; 35:1-10), reducing cerebrovascular infarcts (Vaughan, C J. et al. The evolving role of statins in the management of atherosclerosis. J. Am. Coll. Cardiol. 2000; 35:1-10), anti ischemic properties (Vaughan, C J. et al. The evolving role of statins in the management of atherosclerosis. J. Am. Coll. Cardiol. 2000; 35:1-10; Scalia, R. et al. Simvastatin exerts both anti-inflammatory and cardioprotective effects in apolipoprotein E-deficient mice. Circulation 2001; 103:2598-2603; Llevadot, J. et al. HMG-CoA-reductase inhibitors mobilizes bone marrow-derived endothelial progenitor cells. J. Clin. Invest. 2001; 108:399-405), stabilization of atherosclerotic plaques (Vaughan, C J. et al. The evolving role of statins in the management of atherosclerosis. J. Am. Coll. Cardiol. 2000; 35:1-10), antithrombotic effects (Vaughan, C J. et al. The evolving role of statins in the management of atherosclerosis. J. Am. Coll. Cardiol. 2000; 35:1-10), fibrinolytic activity (Essig, M et al. 3-hydroxi-3-methylglutaryl coenzyme A reductase inhibitors increase fibrinolytic activity in rat aortic endothelial cells. Circ. Res. 1998; 83:683-690), endothelial function (Vaughan, C J. et al. The evolving role of statins in the management of atherosclerosis. J. Am. Coll. Cardiol. 2000; 35:1-10; Scalia, R. et al. Simvastatin exerts both anti-inflammatory and cardioprotective effects in apolipoprotein E-deficient mice. Circulation 2001:103:2598-2603; Ignarro, L J et al. Endothelium-derived relaxing factor produced and released from artery and vein is nitric oxide. Proc. Natl. Acad. Sci. 1987; 84:9265-9269; Gauthier, T W et al. Nitric oxide protects against leukocyte-endothelium interactions in the early stages of hypercholesterolemia. Arterioscler. Thromb. Vasc. Biol. 1995; 15:1652-1659; Radomski, M W et al. S-Nitroso glutathione inhibits platelet activation in vitro and in vivo. Br. J. Pharmacol 1992; 107:745-749), platelet function (Gauthier, T W et al. Nitric oxide protects against leukocyte-endotheliuminteractions in the early stages of hypercholesterolemia. Arterioscler. Thromb. Vasc. Biol. 1995; 15:1652-1659), vascular anti-inflammatory effect (Vaughan, C J. et al. The evolving role of statins in the management of atherosclerosis. J. Am. Coll. Cardiol. 2000, 35:1-10; Scalia, R. et al. Simvastatin exerts both anti-inflammatory and cardioprotective effects in apolipoprotein E-deficient mice. Circulation 2001; 103:2598-2603).

Based on the background described above, related to the inflammatory mechanisms involved in the development of cardiovascular disease, there is a certain parallelism between them and the inflammatory changes responsible for the pathogenesis of periodontal disease. A growing interest in studying the potential relationship between both diseases has been developed in recent decades, suggesting the involvement of common underlying mechanisms that would link periodontal and cardiovascular health. In vitro and in vivo assays have suggested the potential use of statins in periodontal disease; also few retrospective studies show that patients with advanced chronic periodontitis treated with statins improve their evolution. However, no prospective study has confirmed these findings, having not yet elucidated whether statins indeed are useful in the treatment of periodontal disease in humans.

Dyslipidemia and Periodontal Disease.

Cardiovascular disease is the most common cause of mortality worldwide. In a significant number of patients, which can reach up to 40%, it is not possible to identify some of the traditional risk factors. In the search for new risk factors, in addition to hyperlipidemia, the role of infection, within which we can relate periodontal disease, has become important (Jongsung Lim S, Luis Pérez P, Eduardo Guarda S, Alejandro Fajuri N, et al. Enfermedad periodontal en pacientes con síndrome coronario agudo. Rev. med. Chile, 2005 February; 133: 183-189).

Chronic periodontitis is defined as an infectious disease that leads to a slow and progressive loss of tooth attachment associated with bacterial infection (Gamonal J, Mendoza C, Espinoza I, Muñoz A, Urzúa I, Aranda W, et al. Clinical attachment loss in Chilean adult population: First Chilean National Dental Examination Survey. J. Periodontol. 2010 October; 81(10):1403-1410). In turn, gingivitis, a milder version of the same condition, is one of the most common localized inflammatory diseases in the adult population. If left untreated, it can lead to chronic periodontitis, a continuous inflammatory process that results in the irreversible destruction of periodontal tissues. This moderate degree of inflammation could represent a considerable burden on the cardiovascular system, contributing to increased risk of cardiovascular diseases, which have shown to be associated with inflammation (Lindy, O. et al. Statin use is associated with fewer periodontal lesions: A retrospective study. BMC Oral Health 2008; 8:16-23).

Among the most common clinical features of periodontitis are clinical attachment loss (CAL), loss of alveolar bone, periodontal pockets and gingival inflammation, all of which, without treatment, can lead to tooth loss (Gamonal J, Mendoza C, Espinoza I, Muñoz A, Urzúa I, Aranda W, et al. Clinical attachment loss in Chilean adult population: First Chilean National Dental Examination Survey. J. Periodontol. 2010 October; 81(10):1403-1410). In turn, loss of teeth with varying infectious and inflammatory commitment of periodontal tissue, determine the activation and release of numerous inflammatory elements into the bloodstream (Jongsung Lim S, Luis Pérez P, Eduardo Guarda S, Alejandro Fajuri N, et al. Enfermedad periodontal en pacientes con syndrome coronario agudo. Rev. med. Chile, 2005 February; 133: 183-189).

The most severe and acute periodontal disease is present in approximately 8-15% of the adult population; while 35% have moderate to mild signs of the same disease in a chronic version of slow progress. Atherosclerosis is also a very common disease that begins early in life. However, as the latter's progression is usually slow, clinical symptoms or hospitalization are rare before 40 years of age (Buhlin, K. et al. Risk factors for cardiovascular disease in patients with periodontitis. Eur. Heart J. 2003; 24.2099-2107).

Other possible mechanisms explaining the association described between periodontitis and cardiovascular disease may be the release of bacteria, bacterial products or pro-inflammatory cytokines from the chronic periodontal lesion to the bloodstream. These factors could lead to a systemic inflammatory response, representing an ideal profile of risk factors for cardiovascular disease. Thus both diseases have many common risk factors (Buhlin, K. et al. Risk factors for cardiovascular disease in patients with periodontitis. Eur. Heart J. 2003; 24:2099-2107).

Periodontal disease is an infectious disease caused by biofilm (oral flora), located on the surface of the tongue, gums, mucous membranes and teeth surfaces. Periodontal pathogens, invade epithelial cells and connective tissue, causing inflammation and periodontal bleeding. This allows the entry of invasive organisms in the bloodstream and this its transport throughout the body (Karnoutsos, K. et al. Periodontitis as a risk factor for cardiovascular disease. Hippokratia 2008; 12:144-149).

Certain oral bacteria are known as causal agents associated with infectious endocarditis. In addition, bacteremia associated with periodontitis is considered risk factors for coronary heart disease and stroke. It was found that samples of atherosclerotic plaque are often infected with multiple infectious agents, such as *Porphyromonas gingivalis* and *Streptococcus sanguis*, which are common in periodontal disease. It has been shown that endotoxins of bacterial plaque microorganisms are able to penetrate the gingival tissue and enter the bloodstream in sufficient quantities to provoke a specific antibody systemic response (Karnoutsos, K. et al. Periodontitis as a risk factor for cardiovascular disease. Hippokratia 2008; 12:144-149).

Periodontitis leads to systemic exposure of oral bacteria and the resultant production of inflammatory mediators can initiate or support mechanisms associated with the development of atherosclerosis and coronary heart disease (Karnoutsos, K. et al. Periodontitis as a risk factor for cardiovascular disease. Hippokratia 2008; 12:144-149). Moreover, among other complications, this causes a deterioration of the diabetic condition, increases oral infections, generates obstetric complications and in its severe status is associated with systemic inflammation and the dysmetabolic state (Lindy, O. et al. Statin use is associated with fewer periodontal lesions: A retrospective study. BMC Oral Health 2008; 8:16-23).

In periodontal disease, clinical attachment loss (CAL) is related to several periodontal risk factors, among which age is very relevant. The National Institute of Dental Research (NIDR from USA) conducted a study in employed adults during 1985 and 1986, which results were verified in a more recent study (Gamonal J, Mendoza C, Espinoza I, Muñoz A. Urzúa I, Aranda W, et al. Clinical attachment loss in Chilean adult population: First Chilean National Dental Examination Survey. J. Periodontol. 2010 October; 81(10):1403-1410), which showed that the percentage of young adults between 35 and 44 years with at least one site with CAL (clinical attachment loss) was 70% and the percentage of adults between 55 and 64 years with at least two CAL was 90%. Whit prevalence in men than in women (Gamonal J, Mendoza C, Espinoza I, Muñoz A, Urzua I, Aranda W, et al. Clinical attachment loss in Chilean adult population: First Chilean National Dental Examination Survey. J. Periodontol. 2010 October; 81(10):1403-1410).

In turn, in a study conducted in Chile in October 2010 (Gamonal J, Mendoza C, Espinoza I, Muñoz A, Urzua I, Aranda W, et al. Clinical attachment loss in Chilean adult population: First Chilean National Dental Examination Survey. J. Periodontol. 2010 October; 81(10):1403-1410) it was found that periodontal disease is also related to the socio-economic status of the subjects. Those with more education, higher incomes and better living conditions have better oral hygiene and better overall health status compared to those with less education, lower income and living in worse conditions. Smoking and tobacco consumption habits have been confirmed as risk factors for acquiring periodontal disease and other conditions that alter oral health (Gamonal J, Mendoza C, Espinoza I, Muñoz A, Urzua I, Aranda W, et al. Clinical attachment loss in Chilean adult population: First Chilean National Dental Examination Survey. J. Periodontol. 2010 October; 81(10):1403-1410).

The assumption that periodontitis is a disease of old age is no longer tenable, and the current view states that most periodontal destruction seen in the elderly population is only a reflection of the accumulation of disease throughout life, rather than a specific condition for age. Males showed greater periodontal destruction with more CAL compared to women, probably related to poorer oral hygiene, less positive attitudes towards oral health and less initiative to visit the dentist, rather than a specific genetic factor. The relationship between periodontitis and low socioeconomic status is less direct and is rather because patients with more education show more positive attitudes toward oral hygiene, and have better access to timely and quality dental care. The association between smoking and periodontal disease is independent from oral hygiene, age, or other likely risk factors. With respect to diabetes, there wasn't found a significant association (Gamonal J, Mendoza C, Espinoza I, Muñoz A, Urzua I, Aranda W, et al. Clinical attachment loss in Chilean adult population: First Chilean National Dental Examination Survey. J. Periodontol. 2010 October; 81(10): 1403-1410). Concluding the above, the main risk factors for developing periodontal disease are: advanced age, male gender, socio-economic status and smoking.

Statins Applied to Dentistry.

As mentioned before, statins are drugs widely used to reduce hyperlipidemia, atherosclerosis and the diseases associated with these conditions, which in recent times have drawn attention for its many non lipid beneficial effects known as pleiotropic effects.

Anti-Inflammatory Effects of Statins in Dentistry.

Within the powerful pleiotropic effects of statins, one of those who acquire particular importance are anti-inflammatory effects. Periodontitis, as a chronic inflammatory disease, shares some mechanisms with atherosclerosis. In periodontitis, the production of pro-inflammatory cytokines and tissue degrading enzymes is initiated and maintained by oral bacterial infection and its associated immune response, resulting in periodontal tissue destruction. It has been found that statins exert anti-inflammatory and immunomodulatory actions as well as the balance of endothelial dysfunction, which should affect the evolution and severity of periodontal disease (Sakoda, K. et al. Simvastatin decreases IL-6 and IL-8 production in epithelial cells. J. Dent. Res. 2006; 85:520-523).

Significant associations between severity of periodontitis and low HDL levels are demonstrated in a recent study (Buhlin, K. et al. Risk factors for cardiovascular disease in patients with periodontitis. Eur. Heart J. 2003; 24:2099-2107). A relationship between periodontitis and body mass index was also observed. A significant association between CRP and periodontitis in patients with CRP levels above 2.30 mg/l was observed, and a weak but significant correlation between HDL and both, bleeding on probing, and the number of periodontal pockets was found. In turn, the levels of plasmatic IL-6 (proinflammatory cytokine) were higher in patients with periodontitis and the monocyte count, among other factors of inflammation in patients with this disease, was higher than in patients without periodontitis (Buhlin, K. et al. Risk factors for cardiovascular disease in patients with periodontitis. Eur. Heart J. 2003; 24:2099-2107).

This correlation is important because it suggests that periodontal disease can affect the concentration of blood lipids and hence the risk of cardiovascular disease. The study showed that 26% of patients with periodontal disease had HDL≤0.9 mmol/L, compared to 11% of patients without the disease. Moreover, HDL has anti-inflammatory properties and can reduce the adhesiveness of endothelial cells (Buhlin, K. et al. Risk factors for cardiovascular disease in patients with periodontitis. Eur. Heart J. 2003; 24:2099-2107). One explanation for the relationship between periodontitis and low levels of HDL could be that chronic inflammation in the periodontium leads to the release of lipopolysaccharide and proinflammatory cytokines such as IL-1β and TNF, which have the ability to influence lipid metabolism. The mevalonate pathway is involved in regulating the expression of inflammatory cytokines. Therefore, statins have shown to have an anti-inflammatory effect that acts by decreasing production of interleukin-6 and interleukin-8, as a pleiotropic effect. It was demonstrated that simvastatin decreases IL-la production in a dose-dependent manner, which facilitates the production of IL-6 and IL-8, important inflammatory mediators factors (Sakoda, K. et al. Simvastatin decreases IL-6 and IL-8 production in epithelial cells. J. Dent. Res. 2006; 85:520-523).

The Periodontal Inflammatory Burden Index (PIBI), which combines and unifies the data on the depth of periodontal pockets, was found to be 40% lower in patients in treatment with statins compared with patients no taking this drug. This inflammation is expressed at a systemic level, which implies an increase in CRP, identified as a marker of atherosclerosis risk. C-reactive protein (CRP), is an independent predictor of future myocardial infarction and stroke among apparently healthy patients. CRP, produced in the liver in response to stimulation by inflammatory cytokines, seems to have inflammatory effects in the endothelium. It has been demonstrate that statin therapy reduces CRP levels, having an important non-lipid anti-inflammatory effect (Ridker, P. et al. Rapid reduction in C-reactive protein with cerivastatin among 785 patients with primary hypercholesterolemia. Circulation 2001; 103:1191-1193). Accordingly, as statins decrease levels of C-reactive protein, statin use may contribute to the prevention and remission of inflammatory diseases, including periodontal disease (Horiuchi, N. et al. Statins and bone metabolism. Oral Dis. 2006; 12:85-101).

Other studies suggest that statins may have important anti-inflammatory effects at different levels of the inflammatory cascade, such as, at the vessel wall (Ridker, P. et al.

Rapid reduction in C-reactive protein with cerivastatin among 785 patients with primary hypercholesterolemia. Circulation 2001; 103:1191-1193).

Matrix metalloproteinases (MMPs) and tumor necrosis factor (TNF-α) may also play an important role in inflammation. Part of the cardiovascular protective effect of statins seems to come from its anti-inflammatory effect, as the inhibition of MMP-9 and TNF-α, among others, which appear to participate in tissue destruction in chronic periodontitis. In addition, statins may promote the differentiation of osteoblasts caused by stimulating the production of bone morphogenetic protein 2 (BMP-2), which can have an important role in the alveolar bone and in healing and growth of periodontal ligament (Saver, B. G. Are statins associated with decreased tooth loss in chronic periodontitis? J. Clin. Periodontol. 2007; 34:214-219). It was also discovered that statins increase vascular endothelial growth factor, which is known to stimulate bone formation (Ayukawa, Y. et al. Local application of statin promotes bone repair through the suppression of osteoclasts and the enhancement of osteoblasts at bone-healing sites in rats. Oral Surg Oral Med. Oral Pathol. 2009; 107:336-342).

Antibacterial Effect of Statins.

Several studies have shown a link between statin use and decreased risk of sepsis and inflammation (Jerwood, S. et al. Unexpected antimicrobial effect of statinas. J. Antimicr. Chem. 2008; 61:362-364). It was found that pretreatment with atorvastatin did significantly reduce the release of cytokines and neutrophil adhesion to venous endothelium in patients undergoing coronary artery bypass surgery, bypass, or cardiopulmonary graft. Recent work (Jerwood, S. et al. Unexpected antimicrobial effect of statinas. J. Antimicr. Chem. 2008; 61:362-364) suggest a 19% lower risk of sepsis in patients with atherosclerosis who take statins. Patients taking statins at the time they develop pneumonia or other serious infections are less likely to develop sepsis, die of sepsis or develop complications that require admission to intensive care unit. These effects are believed to be due to the known pleiotropic effects of these drugs, including anti-inflammatory, vasodilatory, immunomodulatory and antioxidant effects (Jerwood, S. et al. Unexpected antimicrobial effect of statinas. J. Antimicr. Chem. 2008; 61:362-364).

Bone Promoters Effects of Statins in Dentistry.

Recently, some studies (Wu, Z. et al. The effect of simvastatin on remodelling of the alveolar bone following tooth extraction. Int. J. Oral Maxillofac. Surg. 2008; 37:170-176) have identified the anabolic effects of statins on osteoblastic bone formation. It was found (Wu, Z. et al. The effect of simvastatin on remodelling of the alveolar bone following tooth extraction. Int. J. Oral Maxillofac. Surg. 2008; 37:170-176) that statins induce and accelerate bone formation locally, and cause the early expression of growth factors that regulate angiogenesis, bone cell differentiation and osteogenesis. Even more, these properties of statins may control some aspects of aging, such as osteoporosis and dementia (Wu, Z. et al. The effect of simvastatin on remodelling of the alveolar bone following tooth extraction. Int. J. Oral Maxillofac. Surg. 2008; 37:170-176).

For several years, aminobisphosphonates drugs are approved worldwide for the treatment of osteoporosis. These agents act primarily to decrease bone resorption by inhibiting the enzyme farnesyl diphosphate synthase (one step in the mevalonic acid pathway) (Chuengsamarn, S. et al. Effects of statins vs. non-statin lipid-lowering therapy on bone formation and bone mineral density biomarkers in patients with hyperlipidemia. Bone 2010; 46:1011-1015).

Statins inhibit the same pathway, but in a previous step. Statins can also antagonize osteoclasts by improving the expression of osteoprotegerin. Specifically, statins can activate the function of osteoblasts by increasing synthesis of bone morphogenetic protein-2 (BMP-2). Studies (Chuengsamarn, S. et al. Effects of statins vs. non-statin lipid-lowering therapy on bone formation and bone mineral density biomarkers in patients with hyperlipidemia. Bone 2010; 46:1011-1015) clearly demonstrate that 18 months of treatment with 40 to 80 mg of simvastatin per day, significantly increase bone formation and decrease bone resorption. It has even been suggested that statin use may inhibit the progression of periodontal disease in patients with low alveolar bone mass and osteoporosis (Vaziri, H. et al. Effect of simvastatin administration on periodontitis-associated bone loss in ovariectomized rats. J. Periodontol. 2007; 78:1561-1567). It has been demonstrated that Simvastatin increases trabecular bone volume, bone formation rate and resistance to compression of cancellous bone. However, the successful use of simvastatin to promote bone formation in vivo depends on the local concentration; therefore, continuous efforts have been made to find a suitable delivery system of the drug. Different doses produce different effects and the dose should be prescribed with caution considering the benefits and risks (Vaziri, H. et al. Effect of simvastatin administration on periodontitis-associated bone loss in ovariectomized rats. J. Periodontol. 2007; 78:1561-1567).

According to the aforementioned, the present invention describe the use of statins in patients with periodontal disease showing a significant decrease in the depth of periodontal pockets and/or a general reduction of inflammation in the gingival tissues compared to those patients not taking this drug.

STATE OF THE ART

Document US20050245439A1 discloses a method for treating, preventing or reducing the risk of joint destruction in a subject who suffers from a joint or musculoskeletal disease. The method comprises administering a histone deacetylase (HDAC) inhibitor or in conjunction with other agents, for example, statins, to inhibit degradation and resorption of cartilage and bone in the joint. The product administered in this method can be formulated as a cream, a gel, an ointment, a paste, a mouthwash, a powder, a tablet, a pill, a granule, a capsule, a lotion, a suspension, a liposome formulation, a nanosphere, a patch, a suppository, an enema, a drip infusion, or an injection solution.

Document WO2008005509A2, discloses compositions, methods and kits for altering the properties of a biological surface using particles such as, for instance, calcium based particles in combination with an agent that binds to the biological surface. The particle further comprises an agent, factor or drug, for example, statins. Properties such as color, sheen, texture, strength, and odor of biological surfaces such as teeth and bone are alterable. The composition comprises a dentifrice including a mouthwash, a mouthrinse, a toothpaste, a tooth powder, a tooth hardener, an antiplaque composition, a dental cream, a dental floss, a liquid, a gel, a chewing gum, including a center-filled gum, a confectionery, including mints, lozenges.

Document WO2007061783A1, provides new methods for inducing or promoting bone growth and/or for reducing or preventing bone deterioration in a mammal subject. The inventive methods generally comprise administering to the subject an effective amount of a resolvin and optionally, other compounds, for example, statins. In particular, the inventive methods may be useful for treating or preventing conditions associated with bone degradation, deterioration or degeneration such as periodontal disease, osteoarthritis, and metastatic bone disease and osteolytic bone disease. The compositions of this document are formulated as a preparation selected from the group consisting of solution, suspension, dispersion, ointment, cream, gel, toothpaste, tooth powder, lozenge, salve, chewing gum, aerosol, mouth spray, pastille, sachet, mouthwash, toothpick, tablet, capsule, and dental floss.

Document US20030186933A1 discloses compositions for pharmaceutical and other uses comprising clear aqueous solutions of bile acids which do not form any detectable precipitates over selected ranges of pH values of the aqueous solution and methods of making such solutions. The compositions of the invention comprise water; a bile acid in the form of a bile acid, bile acid salt, or a bile acid conjugated with an amine by an amide linkage; and either or both an aqueous soluble starch conversion product and an aqueous soluble non-starch polysaccharide. The composition remains in solution without forming a precipitate over a range of pH values and, according to one embodiment, remains in solution for all pH values obtainable in an aqueous system. The composition, according to some embodiments, may further contain a pharmaceutical compound in a pharmaceutically effective amount. Non-limiting examples of pharmaceutical compounds include insulin, heparin, bismuth compounds, amantadine and rimantadine.

The aforementioned documents do not disclose compositions based mainly in statins as active compound for preventing and treating periodontal disease, for complementing standard treatment of periodontal disease and for bone regeneration. All the compositions from these documents comprise other active ingredients which provide the biological action, and statins are just optionally and secondary compounds.

SUMMARY OF THE INVENTION

Figure 1:
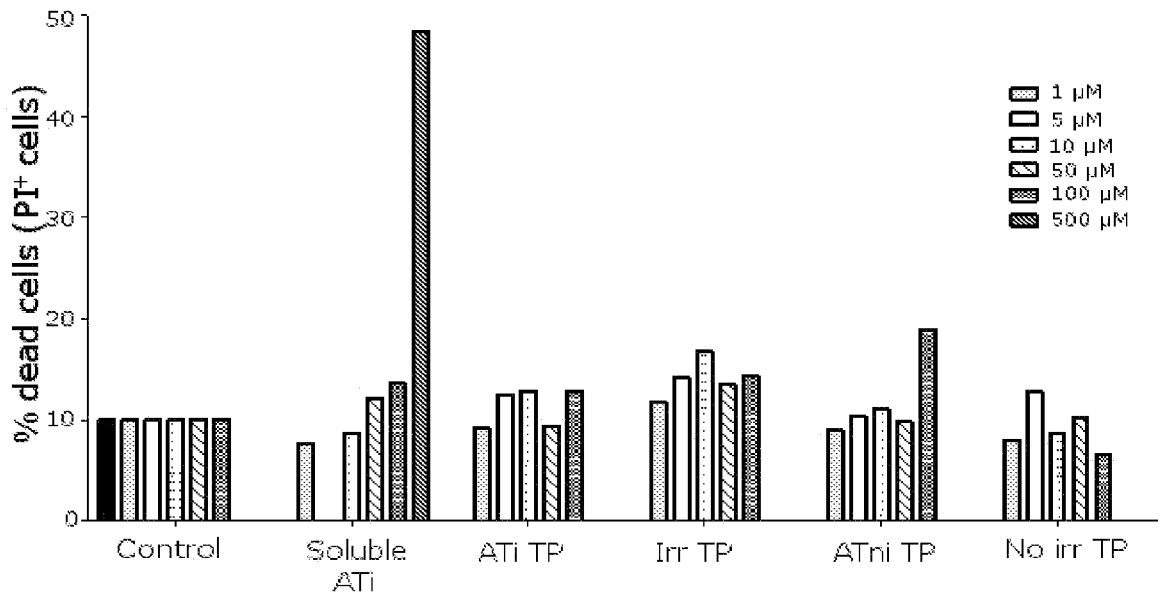
FIG. 1: Cell toxicity evaluation of a fluoride toothpaste prototype medicated with Atorvastatin at 2%. (Example 4).

The present invention discloses topical compositions comprising at least one statin as the main active compound for primary prevention or treatment of periodontal disease, for complementing standard treatment of periodontal disease, and for bone regeneration.

The topical compositions for primary prevention or treatment of periodontal disease, are formulated for example, but not limited to, as toothpaste, mouthwash, tablets to dissolve in the mouth, elements or devices for intraoral slow-release of statins, and dental floss.

The topical compositions for complementing standard treatment of periodontal disease are formulated for example, but not limited to, as gel for being applied in dental trays, and concentrated gel for irrigation of periodontal pockets.

The topical compositions for bone regeneration are formulated for example, but not limited to, fluid (for example in blisters), powder, powder or liquid for preparing a solution, and gel.

The present invention also discloses a method for primary prevention or treatment of periodontal disease, a method for complementing standard treatment of periodontal disease, and a method for bone regeneration, comprising administering the topical compositions in the different formulations to a subject in need thereof.

DETAILED DESCRIPTION OF THE INVENTION

The present invention discloses topical compositions comprising statins as the main active compound for primary prevention or treatment of periodontal disease, for complementing standard treatment of periodontal disease, and for bone regeneration.

In one embodiment, topical compositions of the present invention comprise at least one statin selected among, but not limited to: lovastatin, pravastatin, simvastatin, fluvastatin, cerivastatin, and atorvastatin or pharmaceutical acceptable salts thereof. Topical compositions of the present invention can also comprise one or more pharmaceutically acceptable carriers, vehicles, additives, excipients, solvents, adjuvants, dyes, flavourings, sweetenings, binders, emollients, fillers, lubricants, preservatives, diluents, thickeners, salts for influencing osmoting pressure, buffers, disintegrants, glidants, wettings, humectants, abrasive agents, surfactants, therapeutic agents (such as anticavities, antiplaque, agents for reducing hypersensitivity, and bleaching agents), or combinations thereof.

In a preferred embodiment, the topical compositions of the present invention are used for primary prevention or for treatment of human or animal periodontal disease. In one embodiment, the topical compositions of the present invention for primary prevention of treatment of periodontal disease are formulated for example, but not limited, as toothpaste, mouthwash, tablets to dissolve in the mouth, elements or devices for intraoral slow-release of statins, and dental floss with at least one statin as the main active agent. In another embodiment, when the topical compositions of the present invention are used for primary prevention or for treatment of animal periodontal disease, the topical compositions can also be incorporated for example, but not limited to, into beef, pork, lamb, chicken and/or turkey bones, cartilages or any substance the animal can chew, or into animal feed, such as, for example, but not limited to, cookies and pellet. In a preferred embodiment, the animals are dogs and cats.

In another preferred embodiment, the topical compositions of the present invention are used as complement for the standard treatment of human or animal periodontal disease. In one embodiment, the topical compositions of the present invention used as complement for the standard treatment of periodontal disease are formulated for example but not limited, as concentrated gel for being applied in dental trays and as concentrated gel for irrigation of periodontal pockets with at least one statin as the main active agent. In another embodiment, when the topical compositions of the present invention are used as complement for the standard treatment of animal periodontal disease the topical compositions can also be incorporated for example, but not limited to, into beef, pork, lamb, chicken and/or turkey bones, cartilages or any substance the animal can chew, or into animal feed, such as, for example, but not limited to, cookies and pellet. In a preferred embodiment, the animals are dogs and cats.

In another preferred embodiment, the topical compositions of the present invention are used in human or animal bone regeneration, for example, but not limited, as a concentrated composition with at least one statin as the main active agent, formulated as fluid (for example in blisters), as powder, as powder or liquid for preparing a solution, and as gel. All this formulations are intended for direct application in bone defects or for application through a vehicle with graft materials, membranes and endo-osseous dental implants. In one embodiment the compositions are used for dental bone defects for example, but not limited, from trauma, tumor lesions, cysts, malformations. In another embodiment, the compositions are used in traumatology, for example, but not limited, for surgery for hip implants, osteosynthesis of fractures, spinal surgery (grafts, and fixation in vertebrae, etc.). In another embodiment, when the topical compositions of the present invention are used in animal bone regeneration, the topical compositions can also be incorporated for example, but not limited to, into beef, pork, lamb, chicken and/or turkey bones, cartilages or any substance the animal can chew, or into animal feed, such as, for example, but not limited to, cookies and pellet. In a preferred embodiment, the animals are dogs and cats.

Providing methods for primary prevention or treatment of human or animal periodontal disease is also an objective of the present invention. The method for primary prevention or for treatment of human or animal periodontal disease comprises administering a topical composition selected from, but not limited to, toothpaste, mouthwash, tablets to dissolve in the mouth, elements or devices for intraoral slow-release of statins, and dental floss with at least one statin as the main active agent to a subject in need thereof. In another embodiment, when the method for primary prevention or for treatment is for animal periodontal disease, then the method can also comprises administering a topical composition incorporated for example, but not limited to, into beef, pork, lamb, chicken and/or turkey bones, cartilages or any substance the animal can chew, or into animal feed, such as, for example, but not limited to, cookies and pellet. In a preferred embodiment, the animals are dogs and cats.

Providing methods for complementing the standard treatment of human or animal periodontal disease is also an objective of the present invention. The method for complementing the standard treatment of human or animal periodontal disease comprises administering a topical composition selected from, but not limited to, concentrated gel for being applied in dental trays and as concentrated gel for irrigation of periodontal pockets with at least one statin as the main active agent to a subject in need thereof. In another embodiment, when the method for complementing the standard treatment is for animal periodontal disease then the method can also comprises administering a topical composition incorporated for example, but not limited to, into beef, pork, lamb, chicken and/or turkey bones, cartilages or any substance the animal can chew, or into animal feed, such as, for example, but not limited to, cookies and pellet. In a preferred embodiment, the animals are dogs and cats.

Providing methods for human or animal bone regeneration is also an objective of the present invention. The method for human or animal bone regeneration comprises administering a topical composition selected from, but not limited to fluid (for example in blisters), as powder, as powder or liquid for preparing a solution, and as gel with at least one statin as the main active agent to a subject in need thereof. In another embodiment, when the method is for animal bone regeneration, then the method can also comprises administering a topical composition incorporated for example, but not limited to, into beef, pork, lamb, chicken and/or turkey bones, cartilages or any substance the animal can chew, or into animal feed, such as, for example, but not limited to, cookies and pellet. In a preferred embodiment, the animals are dogs and cats.

INDUSTRIAL APPLICABILITY

The present invention is related to the use of compositions comprising statins as the main active compound in different formulations, applicable in dentistry and medicine, particularly for primary prevention or treatment of periodontal disease for complementing standard treatment of periodontal disease and for bone regeneration.

EXAMPLES

The following examples are meant to illustrate, but in no way to limit, the claimed invention.

Example 1: Formulation of 2% Atorvastatin Toothpaste

For 10 ml:

| | |
|---|---|
| Calcium atorvastatin | 200 mg |
| Menthol | 5 mg |
| sodium fluoride | 5 mg |
| Lutrol gel | 250 mg |

Base gel (enough quantity for) 10 ml

Calcium atorvastatin was dissolved in ethanol. Menthol and sodium fluoride were added. The whole mix was dissolved in lutrol gel and enough quantity of base gel for 10 ml of formulation was added.

Example 2: Evaluation of the Association of Systemic Drug Therapy of Statins in the Periodontal Status for an Adult Population A concurrent cohort study was perform, with two groups of patients, some exposed to statin therapy and some not exposed to statin therapy. Patient submitted to statin therapy received Atorvastatin 20 mg, every 24 hours, indicated as part of a preventive cardiologic therapy.

The eligible patients were those that meet the following inclusion criteria: a) informed consent, b) over 35 years, c) with at least 14 natural teeth in the mouth (excluding third molars), d) have some degree of periodontal disease. The excluded patients were those who: a) had migration plans, b) had presence of limiting disease for understanding the study and its execution or for being hospitalized, c) received periodontal treatment in the last year d) received antibiotic nonsteroidal anti-inflammatory drugs therapy in the last 2 months, e) used calcium channel blockers, phenytoin, cyclosporine, or any associated drug that could affect the gum tissue, f) had an autoimmune pathology.

Measures were taken when starting the study and after 6 months for both groups of patients. The examination included probing depth (PD), clinical attachment level (CAL) and bleeding on probing index (BOP).

PD was defined as the distance from the free gingival margin to the pocket bottom. Periodontal probing was performed to each tooth at 6 sites (mesiovestibular, mediovestibular, distovestibular, mesiolingual/palatal, mediolingual/palatal and distolingual/palatal). CAL was defined as the distance from the cementoenamel junction to the pocket bottom. Periodontal probing was performed to each tooth at 6 sites (mesiovestibular, mediovestibular, distovestibular, mesiolingual/palatal, mediolingual/palatal and distolingual/palatal). BI was determined by assigning a "+" sign to the presence of bleeding on probing in vestibular and/or palatal of the examined tooth and with a "−" sign to the absence of bleeding. Subsequently, "+" signs were added and divided by the total examined sites.

Periodontal Inflamed Surface Area (PISA) was also calculated using data insertion loss, gingival recession and bleeding on probing. The respective periodontal diagnosis was defined through the examination of all teeth present in mouth, excluding third molars.

The classification of patients was made according to clinical criteria proposed by Page and Eke (Page, R; Eke, P; 2007. Case Definitions for Use in Population-Based Surveillance of Periodontitis, Journal of Periodontology July 2007, Vol. 78, No. 7s: 1387-1399) for studies of these characteristics:

0: No presence of moderate and severe periodontitis.
1: Moderate periodontitis: CAL greater than or equal to 4 mm in two or more interproximal sites (not in the same tooth) or at least two interproximal sites with PD greater than or equal to 5 mm.
2: Severe periodontitis: two or more interproximal sites with CAL greater than or equal to 6 mm. and at least one of them with PD greater than or equal to 5 mm.

Only subjects with some level of periodontal disease were considered in the study group, from both disease categories 1 and 2. To observe progression, stability or improvement of periodontal condition, after the observation period of 6 months, the changes that occur in the classification of individuals, between categories 0, 1 and 2 were observed.

Measurements at Gingival Crevicular Fluid Level (GCF).

Upon confirmation of periodontal diagnosis, samplings of GCF were taken by standard procedures. These are described below:

Two sites were selected from each quadrant which PD is higher. After isolating the tooth with cotton balls, supragingival plaque was removed with a curette without touching the gingival margin. Crevicular site was gently dried with air. The GCF was collected with paper cones. The paper points were inserted into the sulcus/pocket until feeling a medium resistance and were left for 40 seconds. Cones contaminated with saliva or blood were excluded. Later the paper cones were placed in a tube. GCF samples were storage at −80° C.

IL-6, IL-10, and C-reactive protein (CRP) were measured as inflammation biomarkers. Measurements were performed through Elisa test. Measurements were performed at the start of the study and after 6 months for both groups of patients, with and without indication of statins.

Results.

It was observed that the group with indication of statins substantially improved their periodontal parameters, both clinical and molecular.

At the clinical level it was observed that patients taking statins reduced the bleeding on probing index (BOP) (considered as the main parameter of periodontal activity) by 60.89%. They also reduced the area of periodontal inflammation measured by the PISA index by 58.66%. At the molecular level, levels of IL-6 in GCF (gingival crevicular fluid) dropped from an average of 4.8 pg/ml in patients without statins use, to an average of 0.47 pg/ml in patients consuming statins. This represents a reduction of 90.1%. Regarding to the levels of IL-10 in GCF, the average in patients not consuming statins was 1.23 pg/ml, whereas no IL-10 could be detected in patients taking statins. The levels of CRP (C-reactive protein) in GCF was reduced by 93% in patients taking systemic statins.

From the above it is concluded that the systemic use of statins contributes to the prevention of periodontal diseases, since it reduces the clinical inflammation of the periodontal tissues, and also contributes even without local treatment. This justifies the development of a topical product for direct application into the mouth, for the complement of periodontal treatment, for subsequent maintenance of periodontal health and also for the prevention of this disease in patients with high susceptibility (smokers, diabetics, immunosuppressed, etc.). All the aforementioned for contributing to the control of periodontal disease through the modulation of the immune response.

Example 3: Clinical Trial

The main objective of this clinical trial was to evaluate the effectiveness of tooth brushing with a toothpaste medicated with 2% atorvastatin (Formulation of Example 1) (2 mg per 0.1 ml) in improving clinical and molecular levels in adult patients after nonsurgical treatment of chronic periodontitis, compared with placebo. Another objectives of this clinical trial were to evaluate specific periodontal clinical parameters such as probing depth (PD), clinical attachment level (CAL), bleeding on probing index (BOP) and periodontal inflamed surface area (PISA) in an adult population suffering from chronic PD, prior and after (1 month later) to non-surgical periodontal therapy, supplemented by oral hygiene instruction indicating atorvastatin 2% medicated toothpaste (Formulation of Example 1) compared with placebo; and to assess patient's biochemical markers in the GCF: IL-6, IL-10, CRP, at baseline and after 1 month.

Materials and Methods.

An atorvastatin 2% toothpaste for brushing was prepared according to Example 1. Medicated prototypes and placebos were dosed in 5 ml syringes indicating each 0.5 ml measures to facilitate dispensing the product and ensure proper use. Thus, each syringe was for 10 doses of toothpaste (10 brushings). 6 syringes were provided to each patient, so that they had enough for a month of treatment, during which they had to brush 2 times a day.

Sample Size.

A clinical trial with two parallel groups (1:1) was conducted, where there were 2 groups of 19 patients each. The estimated sample size was based on the difference in level of integration achieved in the study of Goodson et al (Goodson J M, Haffajee A D, Socransky S S, Kent R, Teles R, Hasturk H, Bogren A, Van Dyke T, Wenostrom J, Lindhe J. Control of periodontal infections: A randomized controlled trial I. The primary outcome attachment gain and pocket depth reduction at Treated sites. J Clin Periodontol 2012, 39: 526-536), with a power of 90%, a significance level of 0.05 two-tailed.

Treatments and Protocols.

Study patients were treated at the Department of Periodontology of the CESA, University of los Andes in San Bernardo.

The two groups underwent non-surgical periodontal therapy consisting of scaling and root planning of all dental groups.

Therapy was supplemented with oral hygiene instruction, indicating patients to brushing with the provided toothpaste, 2 times a day for two minutes each time. Then they were told to spit the toothpaste excesses during 30 seconds, but not to rinse their teeth, or consume liquids or solid foods for at least 30 minutes. A group of 19 patients received the atorvastatin toothpaste 2%, while the other group of 19 patients received toothpaste without the drug to act as a placebo.

Inclusion Criteria.

Patients included in the study were those fully agreeing to participate by signing an informed consent, which has been submitted to and approved, together with the study protocol by the Ethics Committee of the Faculty of Dentistry of the Universidad de los Andes. The identity of the patients was kept confidential and anonymous. The target population consists of 38 adult patients who consult the Service of Periodontology at the University of Los Andes. The eligible patients were those that meet the following criteria: a) gave informed consent, b) had more than 35 years of age, c) had at least 14 natural teeth in mouth (excluding third molars), and d) had some degree of periodontal disease. There were excluded those who: a) related migration plans, b) had presence of limiting disease for the understanding and execution of the study or were hospitalized, c) received periodontal treatment in the last year d) completed antibiotic therapy or Non-steroidal Anti-inflammatory Drugs (NSAIDs) in the last two weeks, e) or were using calcium channel blockers, phenytoin, cyclosporine or any associated drug that may affect gum tissue, f) had autoimmune pathology, g) required antibiotic prophylaxis for periodontal treatment, h) required treatment with NSAIDs for postoperative pain control after the procedure done, i) had statin therapy for dyslipidemia, and j) pregnant patients. Recruitment was done through a consecutive screening of subjects attending the aforementioned service for periodontal treatment.

Measurements of Periodontal Disease.

The enrolled subjects were examined in the CESA (dental clinics) at the University of los Andes, by the same calibrated examiner using basic test instruments and a periodontal probe. The examination includes probing depth (PD), clinical attachment level (CAL) and bleeding index (BI). The PD was defined as the distance from the free gingival margin to the bottom of the pocket. For each tooth it was conducted periodontal probing at 6 sites (mesiobuccal, mediovestibular, distobuccal, mesiolingual/palatal, mediolingual/distolingual, palatal/lingual).

The Clinical Attachment Level (CAL) was defined as the distance from the cement-enamel junction to the fornix of the pocket. For each tooth it was performed periodontal probing at 6 sites (mesiobuccal, mediovestibular, distobuccal, mesiolingual/palatal, mediolingual/distolingual, palatal/lingual). The bleeding on probing index (BOP) was determined by assigning + to the presence of bleeding on vestibular/palatal probing of the tooth examined and with a sign − the absence. Later the + signs were summed and divided by the number of sites examined.

Besides, the PISA (periodontal inflamed surface area) was also computed through an Excel spreadsheet, using data insertion loss, and gingival recession and bleeding on probing. The respective periodontal diagnosis was defined through the examination of all teeth present in the mouth, excluding third molars.

Measurements at the Level of Gingival Crevicular Fluid (GCF).

Once the periodontal diagnosis was confirmed, it was proceed with the GCF sampling. This is described below:

Two sites were selected in each quadrant whose PD is greater. After isolating the tooth in a relative way with cotton swabs, it was proceed to the removal of supra-gingival plaque with curette without touching the gingival margin. The crevicular site was dried gently with triple syringe air. GCF was collected with paper cones. The paper points were inserted in the pocket until feeling resistance and left there for 40 seconds. Cones contaminated with saliva or blood were excluded. Later, paper cones were put into an Eppendorf tube. GCF samples were stored under cold at −80° C.

All samples were sent for analysis to the Research Laboratory of the University of los Andes (CIBRO). These samples were sent under a strictly pre-established protocol.

The following biomarkers of inflammation were measured: IL-6, IL-10, C-reactive protein (CRP) both of R and D Systems™. The biomarkers were measured through Elisa test. Similarly to the clinical evaluation, they were measured at baseline (both groups: with and without statins), and after a month (in both groups: with and without statins).

Bias Control

GCF samples of patients were labeled with numbers by another person, so there is no influence on the researcher when evaluating the markers.

The record of the application of statins was done by a professor at the Faculty of Dentistry, before periodontal clinical evaluation, in order not to influence the researcher.

The allocation to each group was random and there was a sequence concealment.

Analysis Plan:

Continuous variables were described with measures of central tendency, dispersion and position and dichotomous variables were tabulated and described with absolute and relative frequencies according to group. To compare the continuous variables between groups an ANOVA or Kruskal Wallis test was used with a subsequent analysis of multiple comparisons. The effect of treatments was explored through a multilevel linear regression model to evaluate the performance considering the non-independence of the measures at each site.

Results.

After conventional treatment of periodontal disease, all indices showed a clear reduction. In the study group using atorvastatin toothpaste, this reduction occurred in higher percentages.

Patients who used 2% atorvastatin toothpaste for one month (study group) after conventional periodontal therapy improved their periodontal parameters to a greater extent than the control group, which used non-medicated toothpaste.

The rate of bleeding on probing was reduced in 12% higher than in the study group, while inflammation area (PISA) decreased 9.5% more than in the control group.

At the molecular level, it was found that in the GCF (gingival crevicular fluid) IL-6, IL-10 and CRP levels had reductions of 8%, 5% and 11% respectively higher, in the study group (which used 2% atorvastatin toothpaste) compared with the control group (which used a non-medicated toothpaste).

If we analyze the data for the groups of high-risk patients, as the group of smokers and diabetics the reductions in all levels are more pronounced. In the group of smokers the rate of bleeding on probing was reduced by 26% higher than in the study group. While inflammation area (PISA) was reduced by 22% more than in the control group. In the diabetic group the rate of bleeding on probing was reduced by 18% higher in the study group, while inflammation area (PISA) was reduced by 12% more than in the control group.

At the molecular level, in high-risk groups, it was found that in the GCF (gingival crevicular fluid) IL-6, IL-10 and CRP levels had reductions of 10%, 7% and 15% respectively higher in the study group than in the control group.

From the above it is concluded that the use of a medicated toothpaste with 2% Atorvastatin helps to improve the outcome of conventional treatment of periodontal disease. This effect was greater in patients who are predisposed to the disease due to immune dysfunction, such as smokers and diabetic patients.

Example 4: Evaluation of the Immunomodulatory Activity of a 2% Atorvastatin Toothpaste The objective of this assay was to evaluate the immunomodulatory activity of a fluoride toothpaste prototype medicated with Atorvastatin at 2% on the proliferation of lymphocytes T.

The specific objectives of this assay were to evaluate the degree of cell toxicity (cell viability measured in dead % of T cells) and the level of T cell proliferation under a specific stimulus in the presence of:
  a. Control: Peripheral blood mononuclear cell (PBMC)+ Phytohaemagglutinin (PHA) without atorvastatin
  b. Soluble ATi: PBMC+PHA+soluble irradiated Atorvastatin (gamma sterilized). A stock solution of Atorvastatin 5 mg/ml was used. Dilutions were performed in complete RPMI medium 10% FBS.
  c. TP ATi: PBMC+PHA+irradiated Atorvastatin toothpaste (gamma sterilized). Toothpaste containing 2% Atorvastatin (20 mg/ml) was used. Dilutions were performed in complete RPMI medium 10% FBS.
  d. Irr TP: irradiated non-medicated with Atorvastatin toothpaste (gamma sterilized). Dilutions were performed in complete RPMI medium 10% FBS.
  e. ATNI TP: PBMC+PHA+non-irradiated Atorvastatin toothpaste (not sterilized). Toothpaste containing 2% Atorvastatin (20 mg/ml) was used. Dilutions were performed in complete RPMI medium 10% FBS.
  f. No irr TP: Non-irradiated toothpaste (nor sterilized). Dilutions were performed in complete RPMI medium 10% FBS.

Materials and Methods

Cell Toxicity Evaluation.

Human PBMC derived from healthy control donors were stimulated with PHA, 25 µg/ml for 48 hours at 5% $CO_2$, in presence or absence of Atorvastatin (AT) in various formulations: irradiated (ATi) or non-irradiated (ATni) Atorvastatin, soluble or toothpaste. The stimulation was performed in RPMI 1640 medium supplemented with 10% FBS, 2 mM L-glutamine, 100 U/mL penicillin, 100 µg/mL streptomycin. Cells were stained with propidium iodide at a concentration of 1 µg/ml, then the samples were analyzed in a flow cytometer Beckman Coulter XL.

Proliferation of T Cells Evaluation.

Human PBMC derived from healthy control donors were stimulated with PHA, 25 µg/ml, in presence or absence of Atorvastatin (AT) in various formulations: irradiated (ATi) or non-irradiated (ATni) Atorvastatin, soluble or toothpaste. The stimulation was performed in RPMI 1640 medium supplemented with 10% FBS, 2 mM L-glutamine, 100 U/mL penicillin, 100 µg/mL streptomycin. At day 0, the PBMC were stained with probe CellTrace™ Violet as described by the manufacturer and then cultured for 4 days at 5% $CO_2$. Later cells were harvested and stained with anti-CD4 antibody conjugated to FITC and the samples were analyzed by flow cytometer Beckman Coulter XL. P value summary: **0.0011, one-way analysis of variance.

Results.

Figure 2:
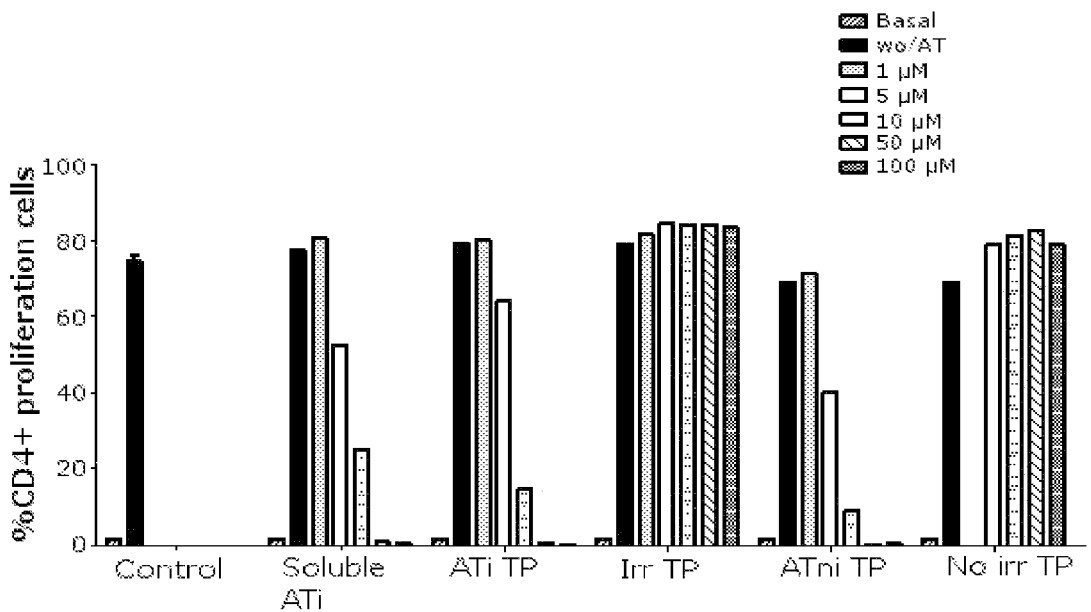
FIG. 2: Proliferation of T cells evaluation of a fluoride toothpaste prototype medicated with Atorvastatin at 2%. (Example 4).

FIGS. 1 and 2 show the results of Cell toxicity evaluation and Proliferation of T cells evaluation.

Concentration of 500 µM in proliferation assays were not used due to the high percentage of cell death, as shown in the viability assay.

None of the formulations used showed increased cellular toxicity; cell viability levels were comparable with the control group.

Significant differences were found between experimental groups. Products containing Atorvastatin (Soluble ATi, Ati TP, and Atni TP) had a clear immunomodulatory behavior, since when applied, reduces immune cell proliferation.

The formulation of toothpaste medicated with 2% Atorvastatin (sterilized and non-sterilized) had an immunomodulatory activity level comparable with a solution of Atorvastatin (5 mg/ml), so it is concluded that its pharmacological activity on cells remained unchanged, discarding interactions with other components.

The invention claimed is:

1. A method for primary prevention or treatment of human or animal periodontal disease, comprising administering a toothpaste composition, by brushing teeth of a human or an animal with the toothpaste composition at least twice daily, wherein the toothpaste composition consists of 2% atorvastatin, and one or more pharmaceutically acceptable carriers, vehicles, additives, excipients, solvents, adjuvants, dyes, flavourings, sweetenings, binders, emollients, fillers, lubricants, preservatives, diluents, thickeners, salts for influencing osmoting pressure, buffers, disintegrants, glidants, wettings, humectants, abrasive agents, surfactants, anticavities, antiplaque, agents for reducing hypersensitivity, bleaching agents, or combinations thereof.

2. A method for complementing standard treatment of human or animal periodontal disease, comprising administering a toothpaste composition, by brushing teeth of a human or an animal with the toothpaste composition at least twice daily, wherein the toothpaste composition consists of 2% atorvastatin and one or more pharmaceutically acceptable carriers, vehicles, additives, excipients, solvents, adjuvants, dyes, flavourings, sweetenings, binders, emollients, fillers, lubricants, preservatives, diluents, thickeners, salts for influencing osmoting pressure, buffers, disintegrants, glidants, wettings, humectants, abrasive agents, surfactants, anticavities, antiplaque, agents for reducing hypersensitivity, bleaching agents, or combinations thereof.

3. The method according to claim 2, for complementing standard treatment of human or animal periodontal disease, further including the steps of formulating a topical composition comprising a concentrated gel of a statin, and applying the concentrated gel in dental trays or using the concentrated gel for irrigation of periodontal pockets.

* * * * *